United States Patent [19]

Yamada et al.

[11] Patent Number: 4,581,365

[45] Date of Patent: Apr. 8, 1986

[54] TRICHLOROACRYLOYL OXIME FUNGICIDES

[75] Inventors: Yasuo Yamada; Junichi Saito, both of Tokyo; Toshio Gotoh, Kanagawa; Osamu Katsumata; Shinji Sakawa, both of Tokyo, all of Japan

[73] Assignee: Nihon Tokushu Noyaku Seizo K.K., Tokyo, Japan

[21] Appl. No.: 557,688

[22] Filed: Dec. 2, 1983

[30] Foreign Application Priority Data

Dec. 17, 1982 [JP] Japan ................. 57-220165

[51] Int. Cl.$^4$ .............. C07D 213/62; C07C 57/02; A01N 43/40; A01N 33/24

[52] U.S. Cl. ............................ 514/351; 546/292; 546/261; 549/510; 564/254; 514/640; 514/514; 514/464; 562/598

[58] Field of Search ............. 546/292, 261; 549/510; 564/254; 260/453.3, 454, 453.8; 514/640, 514, 351, 464; 562/598

[56] References Cited

U.S. PATENT DOCUMENTS

| | | | |
|---|---|---|---|
| 3,733,419 | 5/1973 | Gutman | 260/453.3 |
| 4,059,625 | 11/1977 | Baker et al. | 260/453.3 |
| 4,244,959 | 1/1981 | Freenor, III | 260/453.3 |
| 4,347,372 | 8/1982 | Föry et al. | 260/453.3 |
| 4,388,464 | 6/1983 | Kristinsson et al. | 260/453.3 |

FOREIGN PATENT DOCUMENTS

| | | | |
|---|---|---|---|
| 106553 | 1/1962 | Czechoslovakia | 260/453.3 |
| 0012158 | 6/1980 | European Pat. Off. | 260/453.3 |

Primary Examiner—Henry R. Jiles
Assistant Examiner—Robert C. Whittenbaugh
Attorney, Agent, or Firm—Sprung Horn Kramer & Woods

[57] ABSTRACT

The invention relates to new trichloroacryloyl oxime compounds of the general formula (I)

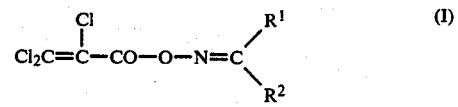

wherein each of $R^1$ and $R^2$ represents a hydrogen atom, a lower alkyl group, a benzyl group, a benzylthio group, a lower alkylthio group, a cycloalkyl group, a halogen atom, a styryl group, a halogenophenylthio group, a naphthyl group, or a phenyl group which may optionally be substituted by at least one substituent selected from the class consisting of a halogen atom, a nitro group, a lower alkyl group, a lower alkoxy group, a phenoxy group, a benzyloxy group, a lower alkylthio group, a thiocyanato group, a di-lower alkylamino group, a halogenopyridyloxy group and a methylenedioxy group, or $R^1$ and $R^2$, together with the carbon atom to which they are bonded, may form an aliphatic ring, said ring being optionally substituted by at least one methyl group, and their use as fungicides. They may be obtained by reacting a trichloroacryloyl halide with an oxime, or by reacting a salt of trichloroacryloyl acid, a formic acid ester halide and an oxime, if appropriate in the presence of a diluent and if appropriate in the presence of an acid binder.

14 Claims, No Drawings

TRICHLOROACRYLOYL OXIME FUNGICIDES

The invention relates to novel trichloroacryloyl oxime compounds, a process for their production, and their use as agricultural fungicides.

It is already known that certain oxime derivatives such as for example, 1,3-dichloroacetone oxime trichloroacetate and 2-chlorocyclohexanone oxime 3-chlorobutyrate, have fungicidal properties (compare U.S. Pat. Nos. 3,733,419 and 4,059,625). The preparation of other oxime derivatives, such as, for example, α-(benzoxazol-2-yl)-α-(O-chloromethylcarbonyl-oximino)-acetonitrile, is known and their use as antidote for herbicides (compare European Patent Application No. 0 012 158).

Now trichloroacryloyl oxime compounds of the general formula (I)

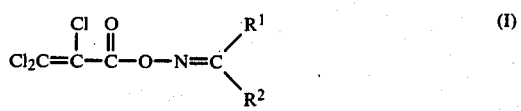

wherein each of $R^1$ and $R^2$ represents a hydrogen atom, a lower alkyl group, a benzyl group, a benzylthio group, a lower alkylthio group, a cycloalkyl group, a halogen atom, a styryl group, a halogenophenylthio group, a naphthyl group, or a phenyl group which may optionally be substituted by 1 to 5 substituents selected from the class consisting of a halogen atom, a nitro group, a lower alkyl group, a lower alkoxy group, a phenoxy group, a benzyloxy group, a lower alkylthio group, a thiocyanato group, a di-lower alkylamino group, a halogenopyridyloxy group and a methylenedioxy group, or $R^1$ and $R^2$, together with the carbon atom to which they are bonded, may form an aliphatic ring having 5 to 8 carbon atoms, said ring being optionally substituted by 1 to 5 methyl groups, have been found.

It has furthermore been found that the new trichloroacryloyl oxime compounds of the general formula (I)

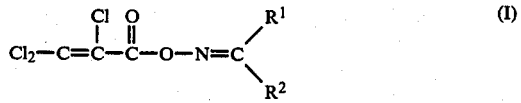

wherein each of $R^1$ and $R^2$ represents a hydrogen atom, a lower alkyl group, a benzyl group, a benzylthio group, a lower alkylthio group, a cycloalkyl group, a halogen atom, a styryl group, a halogenophenylthio group, a naphthyl group, or a phenyl group which may optionally be substituted by 1 to 5 substituents selected from the class consisting of a halogen atom, a nitro group, a lower alkyl group, a lower alkoxy group, a phenoxy group, a benzyloxy group, a lower alkylthio group, a thiocyanato group, a di-lower alkylamino group, a halogenopyridyloxy group and a methylenedioxy group, or $R^1$ and $R^2$, together with the carbon atom to which they are bonded may form an aliphatic ring, said ring being optionally substituted by 1 to 5 methyl groups, are obtained by a process in which (a) an acyl halide of the general formula

wherein Hal represents a halogen atom, is reacted with an oxime of the general formula

wherein $R^1$ and $R^2$ are as defined above if appropriate in the presence of a diluent and if appropriate in the presence of an acid binder or the new trichloroacryloyl oxime compounds according to the invention are obtained by a process in which (b) trichloroacrylic acid derivatives of the formula (IV)

in which M represents an alkali metal atom or hydrogen is reacted with a formic acid ester halide derivative of the formula (V)

in which Hal represents a halogen atom and alk represents a lower alkyl group to from compounds of the formula (VI)

which are reacting in a second step with an oxime derivative of the formula (III) from the compounds of the formula (I) according to the invention, if appropriate in the presence of a diluent and if appropriate in the presence of an acid binder.

It has furthermore been found that the trichloroacryloyl oxime compounds of the formula (I), in which $R^1$ and $R^2$ have the above-mentioned meaning have powerful biological activities, especially fungicidal properties.

Such fungicidal activity can be conveniently applied to their use as agricultural fungicides, and is most suitable for the control of rice blast.

It has also been found that the compounds of this invention have excellent penetrability ascribable to their structural characteristics. In addition to the aforesaid activity, they exhibit a marked control effect against rice blast especially when applied to the surface of, or mixed with, the water in a rice paddy, and therefore, can be used to save agricultural labor.

It has further been found that since the compounds of this invention have low toxicity to warm-blooded animals, and in the concentrations usually employed are not phytotoxic to cultivated plants, they can be used with safety.

The substances according to the invention thus represent an enrichment of the art.

Formula (I) provides a general definition of the trichloroacryloyl oxime compounds according to the invention.

Preferred compounds of the formula (I) are those in which

R¹ and R² independently of one another represent hydrogen, straight-chain or branched alkyl with 1 to 6 carbon atoms, benzyl, benzylthio, straight-chain or branched alkylthio with 1 to 6 carbon atoms, cycloalkyl with 3 to 6 carbon atoms, halogen atoms, in particular fluorine, chlorine, bromine or iodine, styryl, phenylthio which is substituted with 1 to 5 halogen atoms, in particular fluorine, chlorine, bromine and iodine, naphthyl, or phenyl which may optionally be substituted by 1 to 3 same or different substituents which are selected from halogen; nitro, lower alkyl or alkoxy, phenoxy, benzyloxy, lower alkylthio, thiocyanato, di-lower alkylamino, halogenopyridyloxy or methylendioxy (all alkyl parts in the above-mentioned substituents 1 to 6 carbon atoms) or R¹ and R², together with the carbon atom to which they are bonded, may form an aliphatic ring having 5 to 8 carbon atoms, which may be substituted by 1 to 3 methyl groups.

Particularly preferred compounds of the formula (I) are those in which R¹ and R² represent a hydrogen atom; methyl, ethyl, propyl, isopropyl, or n-(iso-, sec-, or tert-)butyl; a benzyl group; a benzylthio group; methylthio, ethylthio, n-propylthio, isopropylthio, n-, iso-, sec- or tert-butylthio, cyclopropyl, cyclobutyl, cyclopentyl or cyclohexyl; fluoro, chloro, bromo or iodo; a styryl group, a halogenophenylthio group having the same halogen atom as exemplified above; a naphthyl group; or a phenyl group which may optionally be substituted by at least one fluoro, chloro, bromo, iodo, nitro, methyl, ethyl, n-(or iso-)propyl, n-(sec-, iso- or tert-)butyl, methoxy, ethoxy, n-(or iso-)propoxy, n-(iso-, sec- or tert-)butoxy, phenoxy, benzyloxy, methylthio, ethylthio, n-(or iso-)propylthio n-(sec-, iso- or tert-)butylthio, thiocyanato, dimethylamino, diethylamino, di-n-propylamino, di-isopropylamino, di-n-butylamino, chloropyridyloxy, fluoropyridyloxy, bromopyridyloxy and methylenedioxy or R¹ and R², together with the carbon atom to which they are bonded, may form a cyclopentane, cyclohexane, cycloheptane or cyclooctane ring which may be substituted by 1 or 2 methyl groups.

If, for example, trichloroacryloyl chloride and benzaldehyde oxime are used as starting substances, the course of the reaction in process (a) according to the invention can be represented by the following equation:

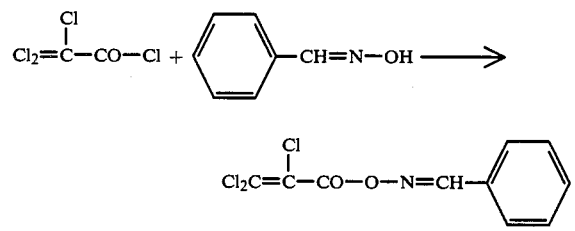

If, for example, the sodium salt of trichloroacrylic acid, the ethyl chloroformate and benzaldehyde oxime are used as starting substances, the course of the reaction in process (b) according to the invention can be represented by the following equations:

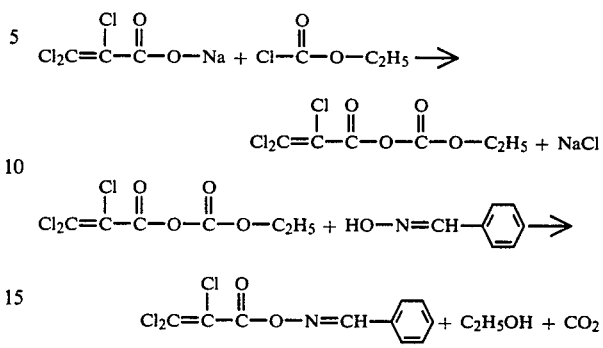

The acyl halides of the formula (II) required as starting substances for process (a) according to the invention are known (compare, for example, Czechosl. Pat. No. 106 553).

Specific examples of the acyl halides of the general formula (II) are trichloroacryloyl chloride and bromide.

Formula (III) provides a general definition of the oximes furthermore required as starting substances for process (a) according to the invention. Most of the oximes of the formula (III) are known (compare, for example, German Pat. No. 952088) or they can be obtained by well-known processes.

Specific examples of the oximes of general formula (III) include benzaldehyde oxime, 1-naphthaldehyde oxime, 2-chlorobenzaldehyde oxime, 3-chlorobenzaldehyde oxime, 4-chlorobenzaldehyde oxime, 2-bromobenzaldehyde oxime, 2,4-dichlorobenzaldehyde oxime, 3,4-dichlorobenzaldehyde oxime, 3,5-dichlorobenzaldehyde oxime, 2,6-dichlorobenzaldehyde oxime, 4-nitrobenzaldehyde oxime, 2-nitrobenzaldehyde oxime, o-tolualdehyde oxime, p-tolualdehyde oxime, 2methoxybenzaldehyde oxime, 2,4-dimethoxybenzaldehyde oxime, 3,4-methylenedioxybenzaldehyde oxime, 3-phenoxybenzaldehyde oxime, 3-benzyloxybenzaldehyde oxime, 3-(5-chloro-2pyridyloxy)benzaldehyde oxime, 4-methylthiobenzaldehyde oxime, 4-thiocyanatobenzaldehyde oxime, 4-dimethylaminobenzaldehyde oxime, α-chlorobenzaldehyde oxime, α-chloro-2-chlorobenzaldehyde oxime, benzylideneacetophenone oxime, α-4-chlorophenylthiobenzaldehyde oxime, acetophenone oxime, acetoxime, α-ethylthio-acetaldehyde oxime, α-benzylthioacetaldehyde oxime, phenylacetone oxime, dicyclopropylketone oxime, cyclopentanone oxime, cyclohexanone oxime, cyclooctanone oxime, 4-methylcyclohexanone oxime, and 2,5-dimethylcyclohexanone oxime.

The trichloroacrylic acid derivatives of the formula (IV) and the chloroformate derivatives of the formula (V) furthermore required as starting substances for process (b) according to the invention are all generally known compounds.

The above processes can be carried out desirably by using a solvent or diluent. For this purpose, all inert solvents and diluents can be used.

Examples of such a solvent or diluent include aliphatic, alicyclic and aromatic hydrocarbons (optionally chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone, and methyl isobutyl ketone; nitriles such as acetonitrile, propionitrile, acrylonitrile; esters such as ethyl acetate, amyl acetate; acid amides such as dimethylformamide and dimethylacetamide; sulfones and sulfoxides such as dimethyl sufoxide and sulfolane; and bases such as pyridine.

The reactions in accordance with this invention may be carried out in the presence of an acid binder. Examples of the acid binder are alkali metal hydroxides, carbonates, bicarbonates and alcoholates which are generally used, and tertiary amines such as triethylamine, diethylaniline and pyridine.

The processes of this invention can be carried out over a broad temperature range. For example, they can be performed at a temperature between about $-20°$ C. to the boiling point of the mixture, desirably between about $0°$ C. and about $100°$ C. Desirably, the reactions are carried out under atmospheric pressure. It is also possible to operate under elevated or reduced pressures.

The active compounds according to the invention exhibit a powerful biological action and can be employed in practice for combating undesired microorganisms. The active compounds are suitable for use as fungicides.

The compounds of this invention have a broad fungicidal spectrum, and can be effectively used against various plant diseases induced by, for example, Archimycetes, Phycomycetes, Ascomycetes, Basidiomycetes and Fungi Imperfecti, and bacteria.

As plant protection agents, the active compounds according to the invention can be used with particularly good success as agricultural fungicides, especially a control effect against rice blast.

As an agricultural fungicide, the compounds of this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

Examples of the agriculturally acceptable adjuvants as referred to herein include diluents (solvents, extenders, carriers) surface-active (solubilizing agents, emulsifiers, dispersing agents, wetting agents), stabilizers, stickers, and synergists.

Examples of the solvents are water, and organic solvents for example hydrocarbons [e.g., n-hexane, petroleum ether, naphtha, petroleum fractions (e.g. paraffin waxes, kerosene, light oils, middle oils, and heavy oils), benzene, toluene, and xylenes], halogenated hydrocarbons (e.g., methylene chloride, carbon tetrachloride, trichloroethylene, ethylene chloride, ethylene dibromide, chlorobenzene and chloroform), alcohols (e.g. methyl alcohol, ethyl alcohol, propyl alcohol, and ethylene glycol), ethers (e.g. diethyl ether, ethylene oxide and dioxane), alcohol ethers (e.g. ethylene glycol monomethyl ether), ketones (e.g., acetone and isophorone), esters (e.g., ethyl acetate and amyl acetate), amides (e.g., dimethylformamide and dimethylacetamide) and sulfoxides (e.g., dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (e.g., pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (e.g., sodium laurylsulfate), arylsulfonic acids (e.g., alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acids esters), and polyhydric alcohol esters (e.g., polyoxyethylene sorbitan monolaurate); and amphoteric surface-active agents.

Examples of other adjuvants include stabilizers; stickers (e.g. agricultural soaps, casein lime, sodium alginate, polyvinyl alcohol, vinyl acetate-type adhesives and acrylic adhesives); dispersion stabilizers [e.g. casein, tragacanth, carboxymethyl cellulose (CMC), and polyvinyl alcohol (PVA)]; and synergists.

The compounds of this invention can be formulated into various forms by methods generally practiced in the production of agricultural chemicals. Examples of such forms include emulsifiable concentrates, oil preparations, wettable powders, soluble powders, suspending agents, dusts, granules, pulverulent preparations, tablets, pastes, and capsules.

The agricultural fungicide of this invention may contain about 0.1 to about 95% by weight, peferably about 0.5 to about 90% by weight, of the aforesaid active ingedient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, the state of occurrence of a plant disease, etc.

If required, the compound of this invention may be used further in combination with other agricultural chemicals, for example insecticides, other fungicides, miticides, nematocides, antiviral agents, herbicides, plant growth regulators and attractants [e.g. organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds], and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring etc.); soil application (mixing, sprinkling, vaporing, pouring, etc.); surface application (coating, banding, powder coating, covering, etc.); and dipping. It can also be used by the so-called ultralow volume spraying method. According to this method, the active ingredient may be included in an amount of 100%.

The rate of application per unit area is, for example, about 0.03 to about 10 kg, preferably about 0.3 to about 6 kg, per hectare. In special cases, however, it may, and sometimes should, be outside the specified range.

According to this invention, there can be provided an agricultural fungicidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling a plant disease, which comprises applying to a pathogenic fungus and/or its habitat and the site of occurrence of the plant disease the compound of general formula (I) alone or in admixture with a diluent (a solvent and/or an extender and/or carrier) and/or surface-active agent and if further required, a stabilizer, a sticker, a synergist etc.

The following examples illustrate the present invention specifically. It should be noted, however, that the invention is not limited to these specific examples alone.

PREPARATION OF EXAMPLES

Example 1

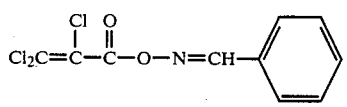

Benzaldehyde oxime (30 g) and 26 g of triethylamine were dissolved in 400 ml of toluene, and 100 ml of a toluene solution of 40 g of trichloroacryloyl chloride was added at less than 20° C.

The mixture was reacted at 50° C. for 2 hours. The resulting triethylamine hydrochloride was separated by filtration, and the organic layer was washed with water and dried. The toluene was evaporated off, and the residue was recrystallized from diethyl ether/n-hexane to give 58 g of the desired benzaldehyde oxime trichloroacrylate as white crystals. The product had a melting point of 79° to 80° C.

Table 1 shows compounds of this invention which were synthesized by much the same method as above.

TABLE 1

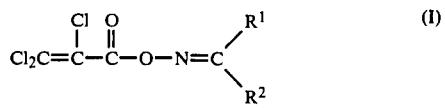

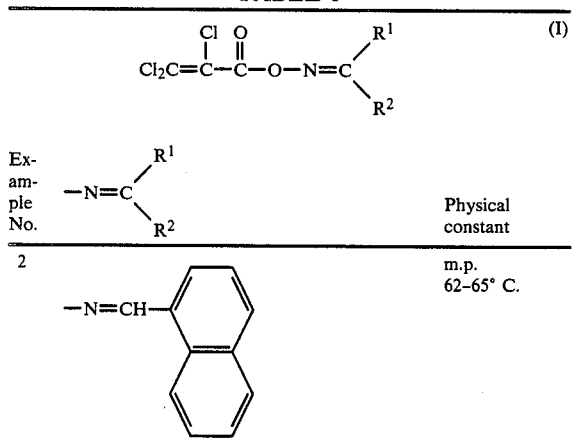

TABLE 1-continued $$Cl_2C=C(Cl)-C(=O)-O-N=C(R^1)(R^2) \quad (I)$$

| Example No. | $-N=C(R^1)(R^2)$ | Physical constant |
|---|---|---|
| 12 | −N=CH−(2-NO₂-C₆H₄) | m.p. 81–85° C. |
| 13 | −N=CH−(4-NO₂-C₆H₄) | m.p. 101–102° C. |
| 14 | −N=CH−(2-CH₃-C₆H₄) | m.p. 62–63° C. |
| 15 | −N=CH−(4-CH₃-C₆H₄) | m.p. 78–79.5° C. |
| 16 | −N=CH−(2-OCH₃-C₆H₄) | m.p. 76.5–77.5° C. |
| 17 | −N=CH−(2,5-di-OCH₃-C₆H₃) | IR: $\nu_{C=O}$ 1745 cm⁻¹ (Nujol) |
| 18 | −N=CH−(3,4-methylenedioxyphenyl) | m.p. 113–114.5° C. |
| 19 | −N=CH−(3-phenoxyphenyl) | IR: $\nu_{C=O}$ 1745 cm⁻¹ (Neat) |
| 20 | −N=CH−(3-benzyloxyphenyl) | m.p. 95–96° C. |
| 21 | −N=CH−[3-(5-chloro-2-pyridyloxy)phenyl] | m.p. 93–97° C. |
| 22 | −N=CH−(4-SCH₃-C₆H₄) | m.p. 105–106° C. |
| 23 | −N=CH−(4-SCN-C₆H₄) | m.p. 136–137° C. |
| 24 | −N=CH−(4-N(CH₃)₂-C₆H₄) | m.p. 110–111° C. |
| 25 | −N=C(Cl)−C₆H₅ | m.p. 43–45° C. |
| 26 | −N=C(Cl)−(2-Cl-C₆H₄) | m.p. 58–60° C. |
| 27 | −N=C(C₆H₅)−CH=CH−C₆H₅ | m.p. 188–189° C. |
| 28 | −N=C(C₆H₅)−S−(4-Cl-C₆H₄) | m.p. 91.5–93° C. |
| 29 | −N=C(CH₃)−C₆H₅ | m.p. 62–63° C. |

TABLE 1-continued $$\underset{\text{(I)}}{Cl_2C=\overset{Cl}{\underset{|}{C}}-\overset{O}{\underset{||}{C}}-O-N=C\overset{R^1}{\underset{R^2}{\diagdown}}}$$

| Example No. | $-N=C\overset{R^1}{\underset{R^2}{\diagdown}}$ | Physical constant |
|---|---|---|
| 30 | $-N=C\overset{CH_3}{\underset{CH_3}{\diagdown}}$ | IR: $\nu_{C=O}$ 1750 cm$^{-1}$ (Neat) |
| 31 | $-N=C\overset{CH_3}{\underset{SC_2H_5}{\diagdown}}$ | IR: $\nu_{C=O}$ 1750 cm$^{-1}$ (Neat) |
| 32 | $-N=C\overset{CH_3}{\underset{SCH_2-\text{Ph}}{\diagdown}}$ | m.p. 74–74.5° C. |
| 33 | $-N=C\overset{CH_3}{\underset{CH_2-\text{Ph}}{\diagdown}}$ | $n_D^{20}$ 1.5445 |
| 34 | $-N=C$(bis-cyclopropyl) | $n_D^{20}$ 1.5440 |
| 35 | $-N=$(cyclopentyl) | $n_D^{20}$ 1.5478 |
| 36 | $-N=$(cyclohexyl) | m.p. 44–44.5° C. |
| 37 | $-N=$(4-methylcyclohexyl) | $n_D^{20}$ 1.5242 |
| 38 | $-N=$(1,4-dimethylcyclohexyl) | $n_D^{20}$ 1.5195 |
| 39 | $-N=CH-$(4-Cl, 3-NO$_2$-phenyl) | m.p. 114–117° C. |
| 40 | $-N=$(cyclooctyl) | $n_D^{20}$ 1.5392 |

FORMULATION EXAMPLES (a) Wettable powder:

Fifteen parts of compound No. 33 of the invention, 80 parts of a 1:5 mixture of white carbon (hydrous amorphous silica powder) and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto a pathogenic fungus and/or its habitat and the site of occurrence of a plant disease.

(b) Emulsifiable concentrate:

Thirty parts of compound No. 5 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto a pathogenic fungus and/or its habitat and the site of occurrence of a plant disease.

(c) Dust:

Two parts of compound No. 10 of the invention and 98 parts of powdery clay are pulverized and mixed to form a dust. It is scattered over a pathogenic fungus and/or its habitat and the site of occurrence of a plant disease.

(d) Dust:

Compound No. 6 of the invention (1.5 parts), 0.5 part of isopropyl hydrogen phosphate, and 98 parts of powdery clay are pulverized and mixed to form a dust. It is scattered over a pathogenic fungus and/or its habitat and the site of occurrence of a plant disease.

(e) Granules:

Water (25 parts) is added to a mixture consisting of 10 parts of compound No. 16 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over a pathogenic fungus and/or its habitat and the site of occurrence of a plant disease.

(f) Granules:

Ninety-five parts of clay mineral particles having a particle size distribution between 0.2 and 2 mm are put in a rotary mixer, and with rotation, 5 parts of compound No. 1 of the invention is sprayed onto the particles to wet them uniformly. The particles are dried at 40° to 50° C. to form granules. The granules are scattered over a pathogenic fungus and/or its habitat and the site of occurrence of a plant disease.

USE EXAMPLES

Example A

Test on efficacy against rice blast by water surface application

Preparation of a test compound

Active compound: 50 parts by weight
Carrier: 45 parts by weight of a 1:5 mixture of diatomaceous earth and kaolin
Emulsifier: 5 parts by weight of polyoxyethylene alkylphenyl ether The active compound, the carrier and the emulsifier in the aforesaid amounts were pulverized and mixed to form a wettable powder. A predetermined amount of the wettable powder was diluted with water to prepare the test compound.

Testing method A

Rice plants (variety: Asahi) were grown in flooded porcelain pots having a diameter of 12 cm, three stalks per pot. In the tillering stage of the rice plants, the test compound of a predetermined concentration prepared as above was poured onto the water surface in the indicated dosages so that it did not directly contact the terrestrial parts of the rice plants. Four days later, a suspension of spores of rice blast fungus (*Piricularia oryzae*) was sprayed onto the rice plants to inoculate the fungus. The plants were maintained for 24 hours in an incubator kept at a temperature of 23° to 25° C. and a relative humidity of 100%. Thereafter, they were transferred to a glass greenhouse kept at a temperature of 20° to 28° C. Seven days after the inoculation, the degree of disease per pot was rated on the following standards, and the control index (%) defined below was calculated.

| Degree of disease | Area of lesions (%) |
| --- | --- |
| 0 | 0 |
| 0.5 | 2 or less |
| 1 | 3–5 |
| 2 | 6–10 |
| 3 | 11–20 |
| 4 | 21–40 |
| 5 | 41 or more |

$$\text{Control index (\%)} = \frac{\left(\begin{array}{c}\text{Degree of disease of}\\\text{a non-treated lot}\end{array}\right) - \left(\begin{array}{c}\text{Degree of disease}\\\text{of a treated lot}\end{array}\right)}{\text{Degree of disease of the non-treated lot}} \times 100$$

The substance shown here is used as a comparison example in the use examples which follow:

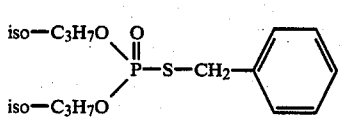

S—benzyl-O,O—di-isopropyl phosphorothioate (Kitazin P)

In this test, a clearly superior activity compared with the prior art is shown for example, by the compounds according to the following preparation examples: 1, 5, 10, 16, 36.

TABLE A

| Example No. | Concentration of the active ingredient (g/m²) | Control index (%) | Phytotoxicity |
| --- | --- | --- | --- |
| 1 | 0.2 | 100 | — |
| 5 | 0.2 | 100 | — |
| 10 | 0.2 | 100 | — |
| 16 | 0.2 | 100 | — |
| 35 | 0.2 | 100 | — |
| Comparison | | | |
| A | 0.51 | 80 | — |

Note:
1. The symbol "—" in the column of phytotoxicity shows that there was no phytotoxicity.
2. A: Kitazin P, 17% granules (commercially available)

The compounds of this invention other than those shown in Example A showed an excellent control effect (a control index of nearly 100%) at active ingredient concentrations of 0.2 g/m² and 0.8 g/m² without any phytotoxicity to rice plants.

Example B

Test on efficacy against rice blast by foliar application

Testing method B

Rice plants (variety: Asahi) were grown in unglazed pots having a diameter of 12 cm. In the 3- to 4-leaf stage, a dilution of a test compound prepared as in Example A in a predetermined concentration was sprayed onto the plants at a rate of 50 ml per three pots. On the next day, a suspension of spores of rice blast fungus (*Pyricularia oryzae*) which had been cultivated artificially was sprayed onto the rice plants. The plants were maintained in a chamber kept at a temperature of 25° C. and a relative humidity of 100% to cause infection. The results were assessed 7 days after the inoculation in the same way as in Example A, and the control index (%) was calculated.

In this test a clearly superior activity compared with the prior art is shown, for example, by the compounds according to the following preparation examples: 3, 5, 6, 8, 9, 10, 14, 15, 16, 23, 25, 29, 33, 34, 35, 37.

TABLE B

| Example No. | Concentration of the active ingredient (ppm) | Control index (%) | Phytotoxicity |
| --- | --- | --- | --- |
| 3 | 500 | 92 | — |
| 5 | " | 100 | — |
| 6 | " | 100 | — |
| 8 | " | 90 | — |
| 9 | " | 92 | — |
| 10 | " | 100 | — |
| 14 | " | 100 | — |
| 15 | " | 94 | — |
| 16 | " | 100 | — |
| 23 | " | 100 | — |
| 25 | " | 92 | — |
| 29 | " | 96 | — |
| 33 | " | 100 | — |
| 34 | " | 95 | — |
| 35 | " | 100 | — |
| 37 | " | 100 | — |
| Comparison | | | |
| A' | 500 | 78 | — |

Note
1. The indication in the column of phytotoxicity is the same as in Table A.
2. Comparison A': Kitazin P, 48% emulsifiable concentrate (commercially available)

It will be understood that the specification and examples are illustrated but not limitative of the present invention and that other embodiments within the spirit and scope of the invention will suggest themselves to those skilled in the art.

We claim:

1. A trichloroacryloyl oxime of the formula (I)

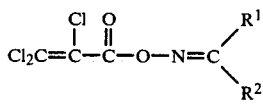

wherein each of R¹ and R² represents a hydrogen atom, a lower alkyl group, a benzyl group, a benzylthio group, a lower alkylthio group, a cycloalkyl group with 3 to 6 carbon atoms, a halogen atom, a styryl group, a halogenophenylthio group, a naphthyl group, or a phenyl group which may optionally be substituted by 1 to 5 substituents selected from the class consisting of a halogen atom, a nitro group, a lower alkyl group, a lower alkoxy group, a phenoxy group, a benzyloxy group, a lower alkylthio group, a thiocyanato group, a di-lower alkylamino group, a halogenopyridyloxy group and a methylenedioxy group, or R¹ and R², together with the carbon atom to which they are bonded, may form an aliphatic ring having 5 to 8 carbon atoms, said ring being optionally substituted by 1 to 5 methyl groups.

2. A trichloroacryloyl oxime according to claim 1 wherein R¹ and R² independently of one another represent hydrogen, straight-chain or branched alkyl with 1 to 6 carbon atoms, benzyl, benzylthio, straight-chain or branched alkylthio with 1 to 6 carbon atoms, cycloalkyl with 3 to 6 carbon atoms, halogen atoms, styryl, phenylthio which is substituted with 1 to 5 halogen atoms, naphthyl, or phenyl which may optionally be substituted by 1 to 3 same or different substituents which are selected from halogen, nitro, lower alkyl or alkoxy, phenoxy, benzyloxy, lower alkylthio, thiocyanato, di-lower alkylamino, halogenopyridyloxy or methylenedioxy, the foregoing alkyl moieties having 1 to 6 carbon atoms, or R¹ and R², together with the carbon atom to which they are bonded, may form an aliphatic ring having 5 to 8 carbon atoms which may be substituted by 1 to 3 methyl groups.

3. A trichloroacryloyl oxime according to claim 1, wherein R¹ and R² represent a hydrogen atom; methyl, ethyl, propyl, isopropyl, or n-(iso-, sec-, or tert-)butyl; a benzyl group; a benzylthio group; methylthio, ethylthio, n-propylthio, isopropylthio, n-(iso-, sec- or tert-)butylthio, cyclopropyl, cyclobutyl, cyclopentyl or cyclohexyl; fluoro, chloro, bromo or iodo; a styryl group; a halogenophenylthio group; a naphthyl group; or a phenyl group which may optionally be substituted by 1 or 2 substituents selected from fluoro, chloro, bromo, iodo, nitro, methyl, ethyl, n-(or iso-)propyl, n-(sec-, iso- or tert-)butyl, methoxy, ethoxy, n-(or iso-)propoxy, n-(iso-, sec- or tert-)butoxy, phenoxy, benzyloxy, methylthio, ethylthio, n- or isopropylthio, n-(sec-, iso- or tert-)butylthio, thiocyanato, dimethylamino, diethylamino, di-n-propylamino, di-isopropylamino, di-n-butylamino, chloropyridyloxy, fluoropyridyloxy, bromopyridyloxy and methylenedioxy or R¹ and R², together with the carbon atom to which they are bonded, may form a cyclopentane, cyclohexane, cycloheptane or cyclooctane ring which may be substituted by 1 or 2 methyl groups.

4. A trichloroacryloyl oxime according to claim 1, wherein such compound is benzaldehydeoxime trichloroacrylate of the formula

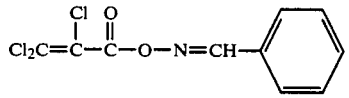

5. A trichloroacryloyl oxime according to claim 1, wherein such compound is 2,6-dichlorobenzaldehydeoxime trichloroacrylate of the formula

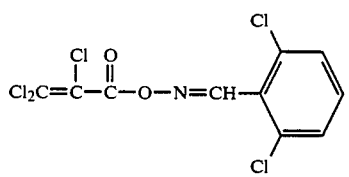

6. A trichloroacryloyl oxime according to claim 1, wherein such compound is 2-methylbenzaldehydeoxime trichloroacrylate of the formula

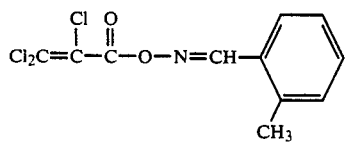

7. A trichloroacryloyl oxime according to claim 1, wherein such compound is 2-methoxybenzaldehydeoxime trichloroacrylate of the formula

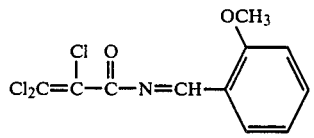

8. A trichloroacryloyl oxime according to claim 1, wherein such compound is 4-thiocyanatobenzaldehydeoxime trichloroacrylate of the formula

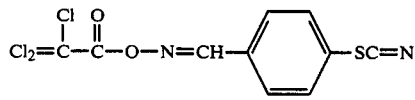

9. A trichloroacryloyl oxime according to claim 1, wherein such compound is α-methylbenzaldehydeoxime trichloroacrylate of the formula

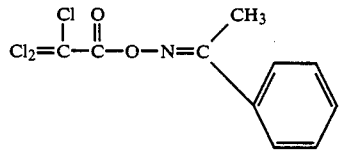

10. A trichloroacryloyl oxime according to claim 1, wherein such compound is 1-benzylthioacetaldehydeoxime trichloroacrylate of the formula 11. A trichloroacryloyl oxime according to claim 1, wherein such compound is cyclohexanoneoxime trichloroacrylate of the formula $$Cl_2=C(Cl)-C(=O)-O-N=\text{cyclohexyl}$$

12. A fungicidal composition comprising a fungicidally effective amount of a trichloroacryloyl oxime according to claim 1 in admixture with a diluent.

13. A method of combating fungi which comprises applying to such fungi or to a fungus habitat a fungicidally effective amount of a trichloroacryloyl oxime according to claim 1.

14. The method according to claim 13, wherein the oxime is
benzaldehydeoxime trichloroacrylate,
2,6-dichlorobenzaldehydeoxime trichloroacrylate,
2-methylbenzaldehydeoxime trichloroacrylate,
2-methoxybenzaldehydeoxime trichloroacrylate,
4-thiocyanatobenzaldehydeoxime trichloroacrylate,
α-methylbenzaldehydeoxime trichloroacrylate,
1-benzylthioacetaldehydeoxime trichloroacrylate, or
cyclohexanoneoxime trichloroacrylate.

* * * * *